United States Patent
Biglieri et al.

(10) Patent No.: US 7,734,324 B2
(45) Date of Patent: Jun. 8, 2010

(54) COMBINED APPARATUS FOR IMAGING THE INNER PART OF A BODY, AND METHOD THEREOF

(75) Inventors: Eugenio Biglieri, Masio (IT); Osvaldo Pugliese, Genoa (IT); Lorenzo Bessi, Florence (IT); Luigi Satragno, Genoa (IT); Luciano Schiavini, Crema (IT)

(73) Assignee: Esaote, S.p.A., Casale, Monferrato (IT)

( * ) Notice: Subject to any disclaimer, the term of this patent is extended or adjusted under 35 U.S.C. 154(b) by 1198 days.

(21) Appl. No.: 10/162,550

(22) Filed: Jun. 6, 2002

(65) Prior Publication Data

US 2002/0188193 A1 Dec. 12, 2002

(51) Int. Cl.
*A61B 5/05* (2006.01)
*A61B 8/00* (2006.01)

(52) U.S. Cl. ......................... 600/407; 600/410; 600/437
(58) Field of Classification Search .......... 600/407–482
See application file for complete search history.

(56) References Cited

U.S. PATENT DOCUMENTS

| | | | | |
|---|---|---|---|---|
| 4,543,959 A | * | 10/1985 | Sepponen | 600/440 |
| 5,146,924 A | * | 9/1992 | Sepponen | 600/410 |
| 5,361,764 A | * | 11/1994 | Reynolds et al. | 600/422 |
| 5,402,786 A | * | 4/1995 | Drummond | 600/410 |
| 5,626,833 A | * | 5/1997 | Schutt et al. | 424/9.52 |
| 5,638,001 A | * | 6/1997 | Vrijheid et al. | 324/318 |
| 5,983,123 A | * | 11/1999 | Shmulewitz | 600/407 |
| 6,070,097 A | * | 5/2000 | Kreger et al. | 600/521 |
| 6,302,579 B1 | * | 10/2001 | Meyer et al. | 378/196 |
| 6,339,717 B1 | | 1/2002 | Baumgartl et al. | |
| 6,480,732 B1 | * | 11/2002 | Tanaka et al. | 600/425 |
| 6,505,063 B2 | * | 1/2003 | Van Den Brink et al. | 600/411 |
| 6,701,176 B1 | * | 3/2004 | Halperin et al. | 600/411 |
| 2001/0047133 A1 | * | 11/2001 | Gilboa et al. | 600/429 |

* cited by examiner

*Primary Examiner*—Long V Le
*Assistant Examiner*—Jacqueline Cheng
(74) *Attorney, Agent, or Firm*—Buchanan Ingersoll & Rooney PC

(57) ABSTRACT

A combined apparatus for diagnostic imaging an inner part of a body, the apparatus including at least a device for imaging and displaying images according to at least two types of beams, waves or signals transmitted toward a body or a part of the body to be examined, the device including a Nuclear Magnetic Resonance imaging and displaying device and an ultrasound imaging and displaying device in an integrated configuration within the same apparatus.

33 Claims, 10 Drawing Sheets

COMBINED APPARATUS FOR IMAGING THE INNER PART OF A BODY, AND METHOD THEREOF

CROSS-REFERENCE TO RELATED APPLICATIONS

This application claims priority under 35 U.S.C. §§119 to IT SV2001A00020, filed in Italy on Jun. 8, 2001; the entire contents of which are hereby incorporated by reference.

BACKGROUND OF THE INVENTION

1. Field of the Invention

The invention relates to a combined apparatus for imaging the internal part of a body, particularly for diagnostic imaging thereof, comprising at least means for imaging and displaying images according to at least one type of beams, waves or signals transmitted by a body or a part thereof to be examined.

2. Description of Related Art

Imaging apparatuses are well-known and include ultrasound imaging apparatuses, Nuclear Magnetic Resonance imaging apparatuses, X-Ray apparatuses, etc. In such type of conventional apparatuses, each apparatus always uses a single type of wave or beam for imaging. From the diagnostic point of view, human body tissues and human body fluid flows provide better or worse different responses in relation to the type of imaging method in use. In order to image with sufficient clearness and accuracy tissues or flows which have an unfavorable imaging behavior, with reference to a specific type of imaging method, arrangements or constructions of imaging apparatuses are often needed which increase the cost and hinder the installation thereof. Hence, for instance, Nuclear Magnetic Resonance imaging apparatuses generally require large magnetic structures. Further, there exists a tendency to provide a separate apparatus for each type of imaging method with considerable purchase costs. It shall be also considered that the physical characteristics of the waves or beams used for imaging have intrinsic limits as regards the capability of imaging certain types of tissues or flows.

In the field of Nuclear Magnetic Resonance imaging, there exists a current tendency toward providing dedicated apparatuses. The peculiar characteristic of these apparatuses is a reduced size of the magnetic structure which allows to considerably limit the weight and dimensions, hence both purchase and installation costs thereof. These apparatuses are constructed in such a manner as to have small housings in which the parts of the body to be examined are to be received. Essentially, instead of housing the patient inside the magnetic structure for a relevant part of his/her body, the dedicated apparatuses may accommodate only small regions of the patient body, like parts of a limb or body, e.g., the region of the knee, elbow, shoulder, etc. This type of Nuclear Magnetic Resonance imaging apparatuses operates with low magnetic fields. In these conditions, imaging of tissues which have unfavorable characteristics with respect to the Nuclear Magnetic Resonance imaging technique in use is even more difficult. In order to obviate this, and to obtain images of a certain quality and usefulness, the drawbacks of small magnetic structures and low fields are compensated by using more complex and longer scanning sequences, i.e., protocols.

Combined apparatuses currently exist for imaging and therapeutic applications, which use, for instance, a Nuclear Magnetic Resonance technique for imaging purposes, in combination with ultrasound probes for therapeutic applications. In these applications, the interference between ultrasound imaging means and therapeutic means is not of substantial importance, since the two techniques do not have to provide mutually related images, whereas the image generally has the only purpose to verify, for instance, the position of the therapeutic tool and/or the effect of the therapeutic application on tissues.

Particularly relevant are imaging apparatuses and method which acquire 3D images of the body under examination. The actual 3D imaging methods combine a certain number of images acquired along a certain number of adjacent scanning planes intersecting the body under examination. Each sectional image, also called a slice, is combined with the other slices relating to their spatial relations in order to organize the information as the section planes of the body under examination along which the images have been acquired, thus obtaining a three dimensional image data set describing the object in a three dimensional data array.

WO 96/32056 discloses a system for multi-dimensional imaging in which an ultrasound system and a x-ray system are combined. This document does not deal with the hardware integration of the two system but limit its disclosure to the techniques for combining the data obtained by the two different imaging systems. The system disclosed in WO 96/32056 is a so called 3D (three dimensional) imaging system.

OBJECTS AND SUMMARY

The invention has an object of providing an apparatus for imaging the inner part of a body, particularly for diagnostic imaging thereof and especially for a so called 3D imaging, which obviates the drawbacks of prior art apparatuses, while allowing to obtain an improved imaging apparatus which has better global imaging functions, a smaller global size, a higher versatility and lower costs.

An embodiment of the invention achieves the above purposes by providing an apparatus as described hereinbefore, wherein at least means for imaging and displaying images according to two types of beams, waves or signals transmitted toward the body under examination or a part thereof are provided together within the same apparatus.

In particular, the apparatus according to one embodiment of the invention includes means for generating, means for receiving, means for univocally relating the information of the waves or beams transmitted back from the body under examination or the part thereof, with a space position of an image unit element (so-called pixel or voxel) and means for reconstructing the image from the array of pixels or voxels obtained thereby, which turn the information of the waves or beams received into brightness and/or color characteristics of the individual pixels, both for Nuclear Magnetic Resonance imaging and for ultrasound imaging.

Hence, the typical elements of an ultrasound imaging apparatus and those of a Nuclear Magnetic Resonance imaging apparatus are integrated in the same apparatus.

Typically, Nuclear Magnetic Resonance imaging apparatuses have a magnetic structure which is composed of a static field generating magnet and of several coils designed to transmit radio-frequency signals for exciting nuclear spins, as well as gradient coils and receiving coils. The magnet, which may be of the permanent, or resistive or superconducting type, defines a cavity for receiving the body under examination or a substantial part thereof, in so-called "total body" magnets, or a limited part of the body or limb in so-called "dedicated" magnets. A patient supporting element, e.g. a patient chair, table/chair or table is associated to the magnetic structure. Total body apparatuses include an electric cabinet which contains all the electronic control and processing/displaying devices. In dedicated apparatuses, a control console is provided, which also has display means. Said console contains the electronics designed to control the magnetic structure, generate nuclear spin exciting signals and gradients, and to process the echo signals picked up by the receiving coils. Moreover, said console contains the electronics for image reconstruction from received signals and for image processing, as well as for the control of display means.

Ultrasound imaging apparatuses generally include a console having integrated or associated display means. The console includes the electronics for controlling an ultrasound probe upon transmission and reception, provided with transmitting and receiving transducers; the electronics for processing the received signals and for reconstructing images; the electronics for controlling the display. The connecting cable/s for one or more ultrasound probes branch off from the console.

In one embodiment of present invention, the apparatus comprises at least one patient supporting means, such as a patient chair, a table/chair, a table, or the like, with a part thereof being provided in the form of a case for accommodating at least a part of the electronic control and/or processing and/or displaying circuits of the Nuclear Magnetic Resonance imaging and/or ultrasound imaging apparatus.

In a particular embodiment, this case consists of a base block for supporting the patient chair, table/chair and/or table, which has the shape of a polyhedron, like a cabinet.

Advantageously, the support means consist of a table/chair with a central base block having the shape of a parallelepiped or the like.

The table/chair may have any construction, and preferably has a table part shorter than a table and an end extension part which may be displaced to several different positions, to be used as a footrest, thereby allowing a downward positioning of the lower part of the legs, or as a table extension, thereby allowing to also support the lower part of the legs on an extension surface of the table part. The armrests may have an identical construction or function.

Particularly, the table may be like the one described in the published patent application EP 913 122.

In accordance with an additional characteristic of an embodiment of the invention, a supervision, control and display console is associated to the table, integrating: the means for controlling the ultrasound apparatus, the display means and the means for controlling them, the means for setting the operating options and the apparatus parameters, possible mass storage means for storing image data and/or hospital file databases.

Advantageously, the console is associated to the table by means of a support structure which is articulated to the table structure and is provided with joints for displacement in different relative positions with reference to the table.

The console has means for connecting, at least partly, the probes and/or sensors of at least a part of the imaging devices, whereas a communication line is provided between the console and the block of circuits dedicated to the control of said sensors and/or said probes, which line connects said probes and/or said sensors to the corresponding block of dedicated circuits.

An additional characteristic of an embodiment of the invention provides that the electronics of the ultrasound imaging device and/or the electronics of the nuclear magnetic resonance imaging device is divided into a part that is specifically designed for the processing of the specific type of transmission/excitation signals and of received signals, i.e., ultrasonic echoes or RF magnetic resonance signals, and into a common image processing and image displaying part, which may process both image data from nuclear magnetic resonance imaging device and image data from the ultrasound imaging device, all data being transmitted on transmission lines or buses.

In this case, the outputs and inputs of the control and processing units dedicated to each specific imaging device, i.e., to the ultrasound imaging device and to the Nuclear Magnetic Resonance imaging device have output and input sections from and toward the control and display console, which encode data and control signals according to identical structures, protocols and transmission/reception parameters which are supported by the communication unit, the so-called communication bus. The electronic units of the console, substantially including the control and adjustment means and the image data processing means also have corresponding input and output sections.

The above has the advantage that it allows to easily integrate the functions generally assigned to two dedicated consoles—one for the ultrasound device and the other for the Nuclear Magnetic Resonance device in a single console, which has the specific control means for the two types of imaging devices and the image processing and displaying means. Hence, the cost and size is further reduced as compared with prior art separate apparatuses.

The above is essentially based on the acknowledgment that when a structured set of image data, e.g. a two-dimensional or three-dimensional data matrix, is constructed by specific and dedicated processing, depending on the different types of signals and by univocal correlation between the individual data and the space location thereof, imaging occurs for the different imaging means with processing procedures which are substantially identical or anyway deriving at least partly from identical algorithms.

The advantages of this configuration of the control, processing and display electronics also allow to possibly provide the integrated apparatus of the invention with additional units for imaging or detecting other physiological parameters. The control means of the additional devices for imaging or detecting physiological parameters and the processing and displaying means may be integrated without affecting the structure of the apparatus, by simply supplying the dedicated electronic units with corresponding means for interfacing them with output and input sections which encode data according to the structure, the protocol and the parameters of the selected communication bus.

Hence, for instance, the integrated apparatus that comprises ultrasound imaging devices and Nuclear Magnetic Resonance imaging devices allows to integrate easily and with no effort, and especially with no changes to the existing structure, except software configuration changes, an X-ray imaging device, and/or an ECG electrocardiograph, or an EGG, EMG or other imaging means.

It shall be further noted that by structuring detected data according to predetermined communication and processing protocols by substantially identical or common means, a high-level integration of the data detected with the different methods is possible.

The embodiment of the invention may further be provided with a magnetic structure for Nuclear Magnetic Resonance imaging which integrates therein at least a portion of the control and processing electronics, thereby increasing the useful space in the housing formed in the table structure or the like.

Referring to the above, the configuration of the control and processing electronics of the different imaging types, allows a mutual integration of the images obtained by said two different types. In fact, when each processing electronics generates image data matrixes having a compatible structure, the latter may be displayed alternately, or in adjacent or overlaid positions on the display screen, thanks to the compatible structuration of data and to the common section of image processing. The information obtained by the different imaging types may be integrated in a better and more detailed image, without having to excessively enhance the individual imaging techniques of the two different types to display particular poorly visible tissues and flows providing lower responses with one imaging type or the other.

In the embodiment of the invention, the integration may be further enhanced to deeper levels, by structuring the dedicated control and processing electronics in such a manner as to also use electronic units having common functions. A particular example may consist, for instance, of the analog to digital conversion section shared by both types of devices. In this case, the analog to digital unit converters of a device may be also used for the other device.

Here, in order to prevent any mutual interference between the two or more imaging devices, a unit is provided to control the imaging procedures on a time-sharing basis. Hence, while one of the imaging devices is enabled, the other is temporarily disabled and vice versa. By using scan speed up techniques, the times of the different imaging steps may be reduced, while ensuring that global imaging times for one and the other imaging device type are relatively short and substantially allow to display the detected images essentially in real time or almost in real time.

In accordance with a further embodiment of the invention, in order to allow the mutual integration of the image data obtained with the different types of imaging devices, advantages may be obtained by providing means for univocal location of the space position of the individual detected image planes with respect to the body under examination or a part thereof. In fact, both ultrasound devices and Nuclear Magnetic Resonance devices image bodies through predetermined slice planes. In order to compare individual images obtained by the same imaging type or by two different imaging types, it is necessary to locate in an accurate and univocal manner the position in space of said slice images with respect to the body or to each other.

To this end, the receiving unit of at least one of the two imaging devices have reference marks that can be univocally located by the other imaging device. To this end, it is very simple to provide the ultrasonic probe with one or more marking elements whose material leaves a definitely and univocally identifiable trace in the image obtained with the other imaging device, for instance small containers of a predetermined shape, filled with water.

Moreover, this characteristic also allows to find the precise orientation of the ultrasonic probe with respect to the body under examination, hence the precise orientation of the slice plane along which imaging occurs.

An ultrasound 3D or three-dimensional imaging technique provides detection of a succession of images over more adjacent different slice planes of the body under examination or a part thereof. The ultrasonic probe is displaced along the body or the part thereof in at least one predetermined direction. The displacement may be a translational or rotary motion of the probe. Said displacement may occur either by mechanical means, in the form of a probe supporting structure which has probe connection means which are supported in such a manner as to allow translation thereof along one or more guides transverse to each other, or said probe connection means may be of the swinging type. Displacements may be controlled either manually or by means of motors. Nevertheless, the probe may also be supported and displaced manually, when this is convenient. In this case, the different slice planes along which ultrasound imaging occurs may not be equally spaced and especially may also not be parallel to each other due to orientation inaccuracies caused by radial displacements.

However, thanks to the marking elements of the probe and to the indication thereof in the Nuclear Magnetic Resonance images, both the precise position of the probe and the exact orientation of the slice plane may be detected. This may be also obtained by providing more aligned marking elements parallel to the axis of the ultrasound waves transmitted to the body under examination, which indicate the orientations of said axis with respect to at least one or more projections on orthogonal planes which subtend the space. In this case, Nuclear Magnetic Resonance imaging may still be performed while the ultrasonic probe is enabled because, if the marking elements provide strong signals, the risk that artifacts may be generated while locating the orientation of the image slice planes of the probe is not relevant. During Nuclear Magnetic Resonance imaging of the body, the probe may be disabled again to prevent the formation of artifacts.

Also, as a further improvement, since ultrasound imaging apparatuses may already have probe position detecting systems which use magnetic fields, it is possible to avoid a real Nuclear Magnetic Resonance imaging of the probe during ultrasound imaging of the body, thereby using the magnetic structure of the Nuclear Magnetic Resonance device as a magnetic sensor for detecting the displacement of the probe which, in this case, would be provided with magnetic or magnetizable elements as marking elements.

Obviously, all the above ultrasonic probe location options may be included in the integrated embodiment of the invention and these may be provided in such a manner as to enable operation and use thereof either alternatively to and in combination with each other.

Yet another characteristic of an embodiment of the invention provides that the Nuclear Magnetic Resonance imaging device is also adapted to three-dimensional imaging, i.e., to detect images composed of a plurality of adjacent slices of the body under examination or of a limited portion thereof.

An example of this device may be similar to the one described and illustrated, for instance, in EP 654 675 and EP 430 322.

Particularly, in dedicated machines, which have small magnetic structures and are designed for imaging delimited parts of the body under examination, real time or almost real time Nuclear Magnetic Resonance imaging techniques may be implemented in the apparatus.

In this case, the electronic control means of the Nuclear Magnetic Resonance imaging device may have imaging sequences or combinations thereof which allow to vary the Field of View, or FOV and/or definition and/or contrast and/or signal-to-noise ratio by limiting these parameters in an alternative or combined fashion to drastically reduce global imaging times. The controls may be such as to allow modification thereof during the scan.

Upon Nuclear Magnetic Resonance three-dimensional scanning of the body under examination or a part thereof, relative displacements must be provided between the magnetic structure and the body under examination or the part thereof. In this case, the means for displacing the magnetic structure and/or the table may be provided with transducers or tracers for detecting the distance from the table. This may be achieved either by mechanical links between the table and the magnetic structure, e.g. one or more guides and/or rotary supports for the table and/or the magnetic structure whereon both the table and the magnetic structure are mounted, or by non contact means, such as proximity sensors or the like.

In combination with the integrated apparatus, the invention also provides several different Nuclear Magnetic Resonance imaging methods.

According to a first method, ultrasound imaging and Nuclear Magnetic Resonance imaging of the same slice of the body under examination are performed in any sequence and at immediately successive time intervals; the received signals for ultrasound pulses and spin echoes are processed separately, whereby virtual images are reconstructed, which are formed by separate image data matrixes; image data matrixes are transmitted to common means for image processing and for controlling the display means whereon ultrasound images, i.e., obtained by ultrasound imaging, and Nuclear Magnetic Resonance images are displayed in alternative, adjacent and/or overlaid configurations.

A further embodiment provides the location of the slice planes whereat ultrasound imaging and Nuclear Magnetic Resonance imaging were performed, and the combination of the two images obtained thereby into a single image, which contains the information obtained by the two separate images.

Yet another embodiment of the method provides the alternate detection of a succession of ultrasound images and of a succession on Nuclear Magnetic Resonance images along a succession of slices of the body under examination; the detection of the positions and orientations of the slice planes along which imaging occurs and the univocal correlation of position data to image data along each slice plane; the reconstruction of three-dimensional matrixes of image data; the transmission of the image data of each three-dimensional matrix of image data obtained with the two imaging modes, to a common image processing and display unit; the combined display of the two images and/or the alternate display and/or the adjacent display of the two images.

In accordance with a variant of the method, the images relating to each slice plane may be displayed in adjacent, alternate or combined positions, immediately or after a very short time from each scan, thereby obtaining a real-time adjacent, alternate and/or combined display of the images detected by ultrasound imaging means and by Nuclear Magnetic Resonance imaging means, along each slice of the body under examination.

According to a further embodiment of the invention, the spacing distances between the slice planes along which slice images are obtained, are different depending for the two imaging types, namely magnetic resonance or ultrasound imaging. The spacing distances between the slice planes along which a slice image of the body under examination or a part thereof is obtained, may be varied based on the closeness of said slice planes to a particular region or interest or non-interest of the body under examination and to a different or equal extent for each of the two imaging types.

Furthermore it is possible to provide that for each imaging type, the imaging parameters are changed between a slice image and the next slice image or for each imaging step with respect to the preceding one and within the same slice image.

In combination therewith, an embodiment of the invention may include the use of contrast agents for ultrasound imaging applications.

In combination therewith or as an alternative thereto, the use of contrast agents for Nuclear Magnetic Resonance imaging applications may be provided.

Advantageously, an embodiment of the invention includes the injection of contrast agents for ultrasound imaging only and/or for Nuclear Magnetic Resonance imaging only, or the injection of mixtures of contrast agents for ultrasound imaging and/or for Nuclear Magnetic Resonance imaging applications.

Contrast agents for ultrasound imaging are made of microbubbles, whereas contrast agents for Nuclear Magnetic Resonance imaging are made of paramagnetic molecules. In this case, in addition to a simple mixture within the same carrier for said contrast agents, the carrier itself may be provided with paramagnetic characteristics so as to have contrast functions for Nuclear Magnetic Resonance imaging. Paramagnetic molecules may be also encased in microbubbles.

The combined use of contrast agents for ultrasound imaging and of those for Nuclear Magnetic Resonance imaging has a considerable advantage. Typically, high quality Nuclear Magnetic Resonance imaging sequences, i.e., having a high resolution, a high contrast and an optimized signal-to-noise ratio are relatively long, whereby it is difficult to determine the moment in which the contrast agents for Nuclear Magnetic Resonance imaging reach the region under examination of the body. The result of a long imaging sequence may be that, when it ends, the contrast agent may be no longer present in a sufficient amount in the region under examination. In these conditions, a new injection of the contrast agent, i.e., another invasive procedure on the patient, is required.

With the ultrasound imaging device, which operates in a more rapid manner, the perfusion of the specific contrast agent may be detected in a much easier manner, whereby more accurate and specific information may be obtained on the instant in which the contrast agents for Nuclear Magnetic Resonance imaging perfuse the region under examination, thereby obviating the need to repeat the invasive process of contrast agent injection.

Even more accurately, it is possible to determine the instant in which perfusion of the region under examination by contrast agents is complete, by detecting physiological parameters of the heart cycle of the patient and by using them to determine the flow of body liquids within the secondary vascular system, i.e., at the capillary level. This additional characteristic of the method also allows implementation of imaging methods like stress echo or the like.

According to still other embodiments of the invention, the integration of several different imaging types into a single Nuclear Magnetic Resonance imaging apparatus allows to provide a section for storing all data relating to a patient, which comprises all the information obtained by the different imaging and physiological parameter detection methods. This allows to automatically obtain a complete database of a considerable number of examinations for each patient.

In order that data obtained with other devices or images may be integrated in said diagnostic database, a data entry unit is provided in combination with said integrated apparatus, which may comprise, in a combined or alternative manner, means like a keyboard, a scanner, or the like.

The embodiment of the invention provides for the detection of a physiological parameter and the control of the enabling functions for one or both imaging types based on the curves or values of said parameters. Particularly, the detected physiological parameter is an electrocardiogram and the imaging by one or both the imaging types is enabled at identical or different phases or times of the heart cycle.

BRIEF DESCRIPTION OF THE DRAWINGS

The characteristics of the invention and the advantages derived therefrom will appear more clearly from the following description of a few non limiting embodiments, illustrated in the annexed drawings, in which.

DETAILED DESCRIPTION OF THE PREFERRED EMBODIMENTS

Figure 1:
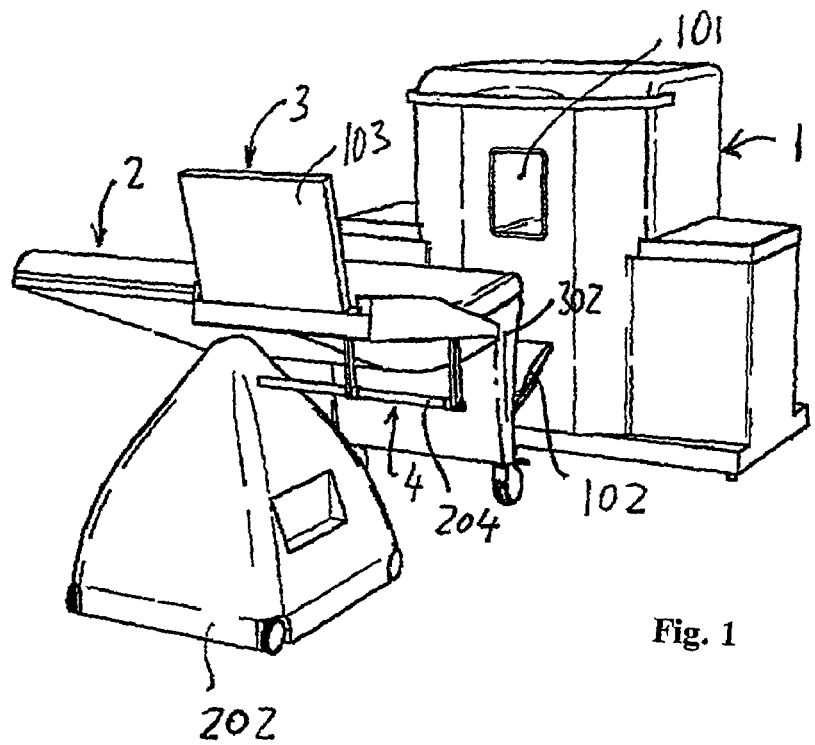
FIGS. 1 and 2 are two perspective views, in two different directions, and with the table in different orientations, of an integrated ultrasound and Nuclear Magnetic Resonance imaging apparatus.
Figure 2:
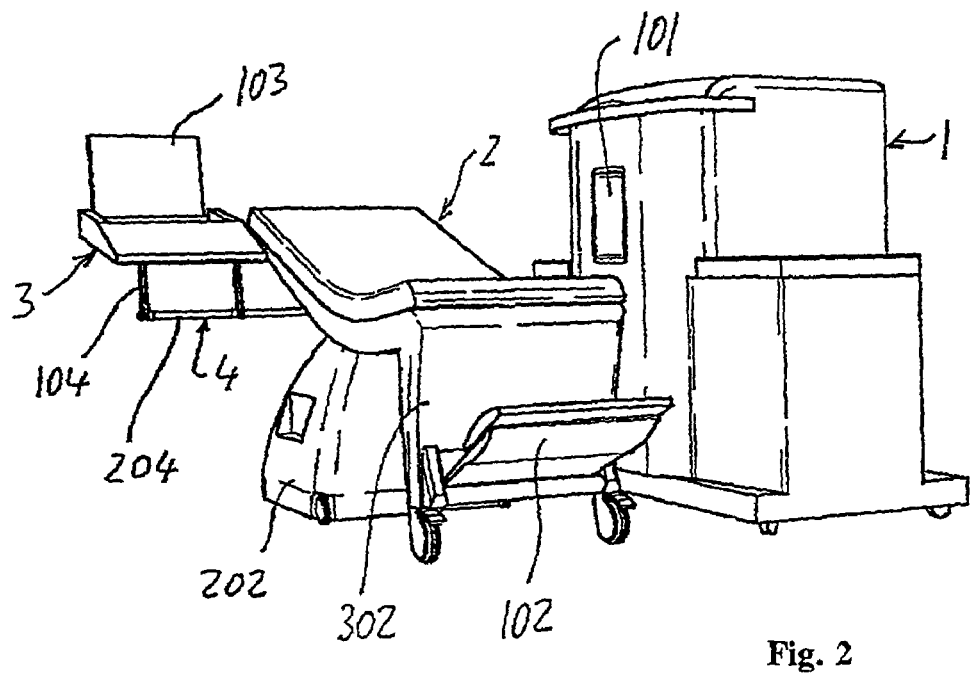

With reference to FIGS. 1 and 2, an integrated apparatus for ultrasound imaging and Nuclear Magnetic Resonance imaging comprises a Nuclear Magnetic Resonance imaging device and an ultrasound imaging device. The Nuclear Magnetic Resonance imaging device comprises a magnetic structure generally denoted as 1, which includes a permanent, resistive or superconducting magnet for generating a static field in a cavity 101 designed to receive a part of the patient body; coils for transmitting radio-frequency pulses for exciting nuclear spins, gradient coils for applying selecting and phase and frequency encoding gradients and receiving coils. All these elements are known per se and are not shown in detail.

In FIGS. 1 and 2, the magnetic structure 1 is contained in a separate case and has a peripherally closed annular shape, with two opposite open sides. A patient table 2, in the form of a table/chair is associated to the magnetic structure 1. Particularly, the table is shorter than the patient body and, in the portion associated to the lower limbs, substantially reaches the knee level, but is able to extend beyond it by a footrest element 102 which may be displaced to various positions, for instance to a lowered and tilted position parallel to the ground with a footrest function, or to a lowered and vertically tilted position against the end side of the table or even to a position in which it extends and completes the surface of the table. A detailed construction example of a table of this type is provided in the published patent application EP 913 122.

Particularly, the table is mounted on an intermediate carriage which consists of a cabinet-like element 202. At one of its end sides, particularly the one associated to the lower limbs, the table has a vertical leg 302, also in the form of a carriage, which extends substantially all along the table, thereby having the function of a pair of traditional legs.

A control console 3 is associated to the patient table 2, particularly but without limitation to the end opposite to the one associated to the lower limbs.

The control console 3 has an upper surface with the different ultrasound imaging controls and advantageously an ultra-slim display 103, e.g. a liquid crystal display, which is articulated to the console 3 in such a manner as to allow it to be tilted to a lifted operating position and to a rest position in which it lays over the upper face of the console 3.

The control console 3 is secured to a support structure 4 formed by swinging arms 104 and supporting and sliding beams 204, in such a manner that it can be displaced relative to the vertical level, swung forward and rearward, and translated transverse to the longitudinal axis of the table 2.

Figure 3:
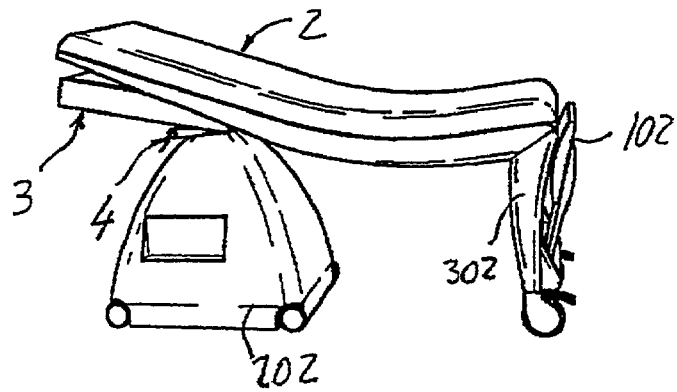
FIGS. 3 to 5 are different perspective views of the apparatus as shown in FIG. 1, in which the magnetic structure of the Nuclear Magnetic Resonance imaging device is omitted, and the console is shown in different operating and rest positions.
Figure 4:
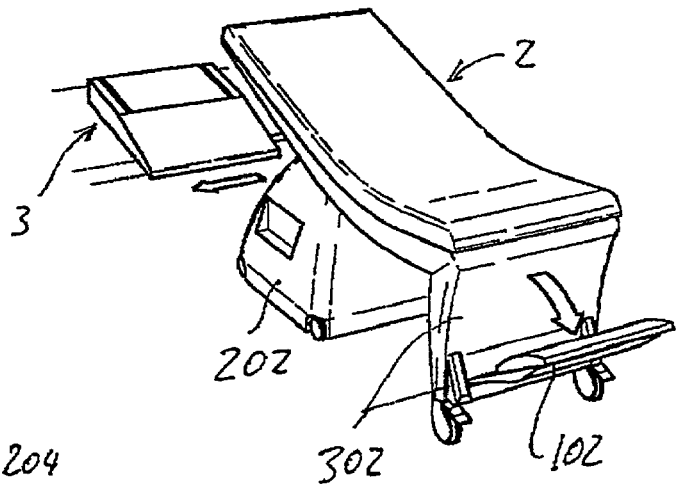
Figure 5:
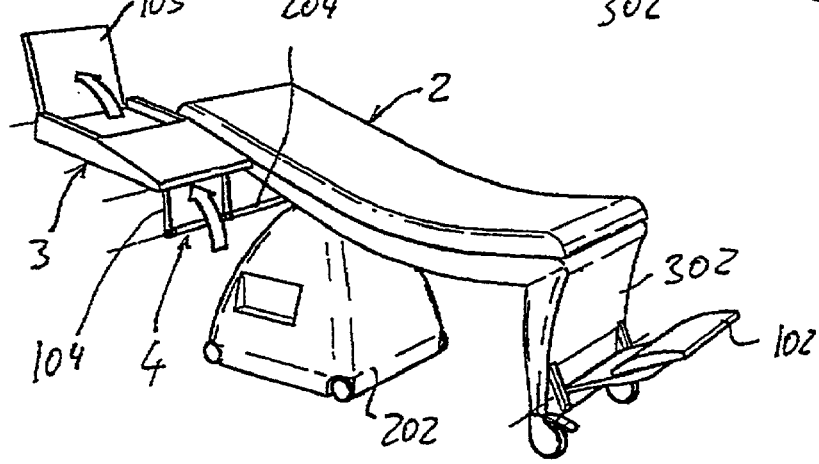

These displacements may be obtained by using any support structure construction, depending on the structure and on the aspect of the table. In the embodiment as shown in the Figures, and with particular reference to FIGS. 3 to 5, the support structure 4 of the console 3 has at least one transverse support guide 204 for transverse sliding, for example extending telescopically or as a rod sliding in slide supports, whereon at least two swinging arms 104 are mounted, which are spaced in the axial direction of the guide 204, and are articulated by their opposite ends to the case of the console 3. The guide 204 may be secured to the lower side of the table 2 by one or more additional vertical and/or longitudinal guides (with reference to the longitudinal axis of the table) and/or with rotary joints according to a vertical axis. The two arms 104 may themselves be secured to the console case 3 to pivot about it with the interposition of a rotary joint for the rotation of the console 3 with respect to a vertical axis. Also, the guide 204 may slide in the transverse direction to such an extent as to allow the console to slide independently on one side or the other of the table 2. As an alternative to the illustrated means, the console may be supported by a jointed arm which may have one or more successive arm sections, connected to each other by spherical or cardan joints, and is fastened to the structure of the table. The jointed arm may be fabricated as is known, for instance for display supporting arms, or the like, with the appropriate changes required by the conditions of displacement of the console 3 relative to the table 2. Advantageously, both the illustrated structure 3 and the possibly provided jointed arm have cavities wherein the wires for connecting the console 3 to other electronic units associated to the imaging devices may pass and be housed.

Thanks to the above construction, the console 3 may be displaced to any position relative to the table 2. Particularly, there are provided an operating position adjacent to one of the sides of the table 2 and a rest position, in which, after tilting the display into the rest position, against the upper surface of the console, the latter may be completely displaced under the surface of the table.

Thanks to this construction, besides ensuring the highest operational convenience, the retractable position of the console within the size of the table allows to reduce the damaging risks, for instance, while displacing the console, and to prevent any hindrance to the freedom of movement of the personnel when intervening on the patient.

With reference to the above construction, the ultrasound imaging device comprises a probe 5 which is connected by a cable to the console or to the control and processing electronics contained inside the cabinet-like support 202 of the table 2.

Here, in order to maintain a relatively limited size of the console 3, the cabinet-like base 202 of the table 2 is provided in the form of an electrical cabinet for housing at least a part or all of the processing electronics of at least the ultrasound imaging device.

According to an advantageous embodiment, the electronics is appropriately divided between the console 2 and the cabinet-like base 202. Particularly, the base 202 contains the typical electronic circuits, specifically dedicated to the control of the ultrasonic probe for the transmission of ultrasonic waves, focusing thereof and reception of reflected waves, the reconstruction according to the focusing rule and the processing of received signals as regards the extraction of data useful for imaging and correlation thereof to a precise space position and to a precise and unique pixel of the image to be displayed. Moreover, these circuits may also comprise all the sections for filtering and for processing the data extracted from the received signals with various processing modes, such as those known as B-Mode, Harmonic Imaging, Doppler, Color Doppler and other data processing and extraction modes. When devices for detecting other data or physiological parameters, e.g. an electrocardiogram are provided, the cabinet 202 may also contain the control and processing units of these devices and possibly the units for synchronizing the signal of the electrocardiogram or other devices, for instance with the electronics of the ultrasound imaging device, such as in the apparatuses known as "stress ultrasound imaging" or the like.

On the other hand, the console 3 includes the electronic circuits for controlling and setting the ultrasound imaging modes, the circuits for image processing and controlling the display means and the means for setting the display and detection controls, such as the selection of imaging modes, amongst the modes mentioned above (B-Mode, Harmonic Imaging, Doppler, Color Doppler, and other data processing and extraction methods).

Advantageously, according to a preferred embodiment, the dedicated circuits of the cabinet 202 and those of the console 3 communicate with each other via communication interfaces which encode the data to be exchanged between the console 3 and the dedicated control and processing circuits contained in the cabinet with a common structure, for instance a so-called bidirectional communication bus.

Mass storage means may be also associated to the console 3 or the cabinet 202, such as hard disks, or the like, means for reading or writing removable data storage media, such as floppy disks, CR-Rom, CD-R, CD-RW and/or flashcard memories or the like, and/or other output peripherals, such as printers and/or other data entry peripherals, such as scanners or the like.

Advantageously, the console 3 has a microprocessor unit, the functions thereof being implemented in software form.

This structure may be easily used to also integrate, in the apparatus of the invention, a program for processing, storage and centralized control of the diagnostic data of the patient, obtained either through the specific analyses performable by the integrated apparatus or through other apparatuses, which may be entered in the patient diagnostic data control program through the various data entry means as mentioned above.

With reference now to the Nuclear Magnetic Resonance imaging device, the latter generally comprises, besides the magnetic structure 1, circuits for generating the excitation sequences and for capturing images and circuits for receiving nuclear spin echoes, which contain the information, i.e., the data for image reconstruction, as well as circuits for reconstructing images, i.e., for extracting image data from received signals and for relating said data to the space location wherefrom it is transmitted, hence to an image pixel. Further, the device comprises, like the ultrasound imaging device, circuits for controlling and setting the modes of the Nuclear Magnetic Resonance imaging device, and circuits for processing, display and storage of reconstructed images.

All the above circuits may be provided in a separate console (not shown in detail). Nevertheless, by using the same circuit configuration as the ultrasound imaging device, the specific part for controlling the magnetic structure and the associated units like excitation coils, gradient coils, etc., and the specific part designed to receive echo signals, to reconstruct and extract image data and relate it to a specific pixel of an array of image pixels, may be housed wholly or partly in the case of the magnetic structure 1 and/or wholly or partly in the cabinet 202, whereas the image processing means, the display control means, the Nuclear Magnetic Resonance imaging command entry means are housed in a separated console (not shown) and/or integrated in the console 3.

Here, the processing and control electronics of the Nuclear Magnetic Resonance imaging device should be provided with a communication interface, i.e., a bidirectional bus for communication with the console 3, which is of the same type as the one used for the control and processing electronics of the ultrasound imaging device.

By this arrangement, the means for image processing and display control may be the same as used in the ultrasound imaging device.

Mass storage means, data entry means, like scanners or the like, for entering data detected by other separate devices and/or data transmission means, like printers or the like may also be shared by the two types of devices.

If the ultrasound imaging device also comprises an ECG unit, the latter may be also interfaced with the Nuclear Magnetic Resonance imaging device, like the ultrasound imaging device, through means for synchronizing resonance imaging with the physiological parameters detected by the ECG.

According to an additional characteristic, the console 3 may have image processing means which combine images of the same section obtained by the ultrasound imaging device and by the Nuclear Magnetic Resonance imaging device. In this case, the advantage consists in the possibility to mutually combine the information of the image obtained by ultrasound imaging and that obtained by Nuclear Magnetic Resonance imaging. Besides obtaining better and more complete results, this combination option may allow to use imaging modes of a reduced duration and complexity for both devices, since even the characteristics that are hardly visible through an imaging method may be visible through the other imaging method.

The combination may be simply obtained by displaying the two images obtained each with one of the two imaging methods sequentially or side by side, or by overlaying the two images, or even by a real combination and mutual integration of the image data obtained by the two imaging modes.

Since the simultaneous use of the two imaging methods may cause adverse effects on one of the two imaging modes, e.g. the presence of ultrasonic transducer power may generate noise which cause the formation of artifacts in the Nuclear Magnetic Resonance imaging signals, the two devices are arranged to be operated in fast alternate succession, on a time-sharing basis. To this end, the console 3 has means for entering time sharing parameters, and a control unit is provided which, based on said parameters, controls the alternate operation of said two imaging devices.

Nevertheless, the two modes may be also used in combination, for instance with the help of contrast agents which are caused to burst or be destroyed by the power provided by the ultrasonic probe, whereas imaging is performed by Nuclear Magnetic Resonance in these conditions of the contrast agents.

A further embodiment of the invention provides an ultrasound imaging device adapted for three-dimensional imaging, particularly obtaining a succession of slice images taken along different adjacent slice planes of the body under examination or a part thereof. In this case, the ultrasonic probe 5 may be displaced essentially parallel to itself in a direction transverse to the scan plane of the slice image. This displacement may be a translational motion in a rectilinear direction or an oscillation about an axis which coincides with the origin of the scan plane.

The probes or transducers may traditionally be displaced manually, or on slides, carriages or movable supports either manually or by motor-driven actuators. The displacement of probes 5 is generally detected with various methods, to be used either separately and alternately or in any combination.

Figure 9:
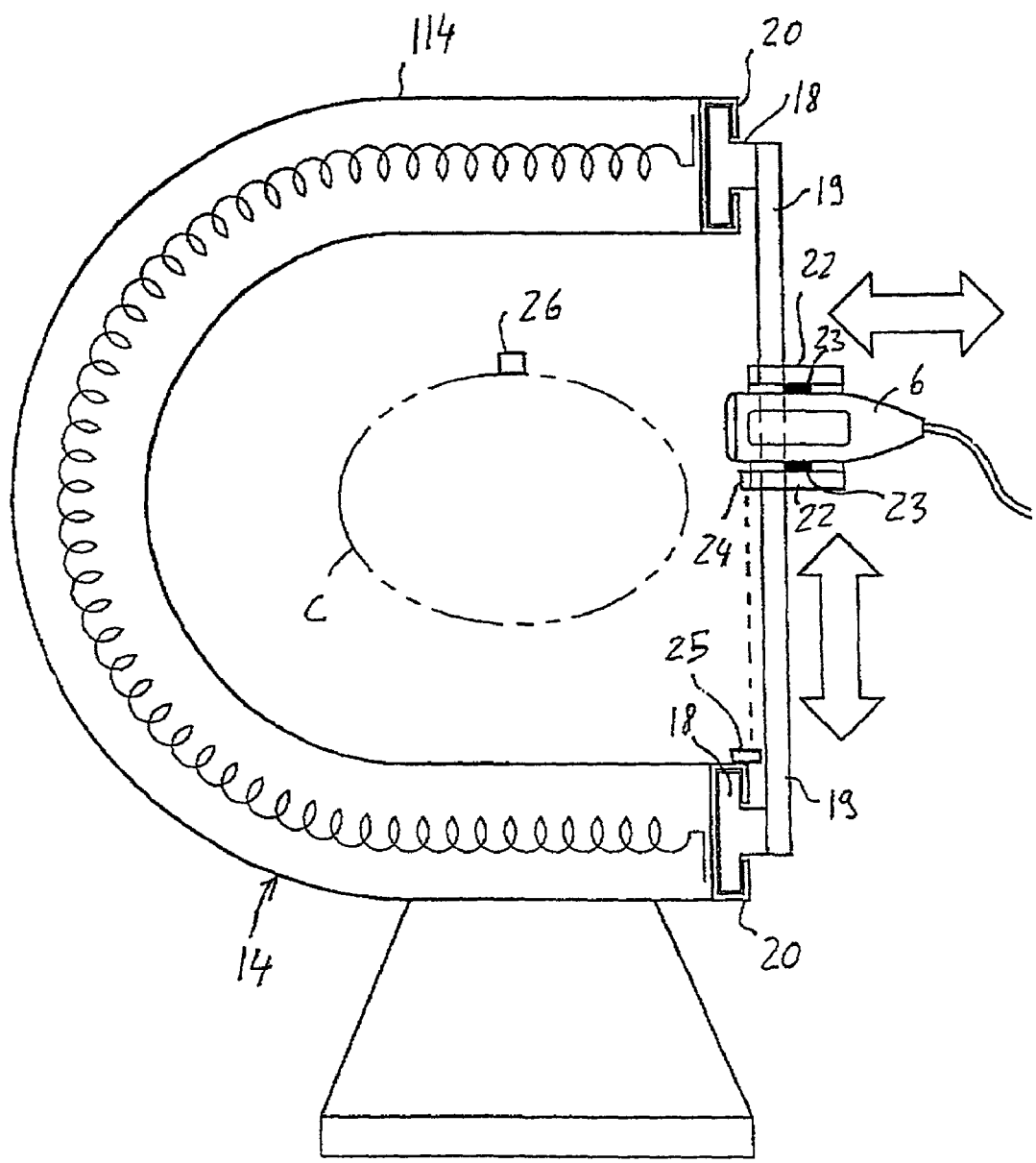
FIG. 9 shows a detail of a C-shaped receiving coil which bears slide support means for reading the position of an ultrasound imaging probe.
Figure 10:
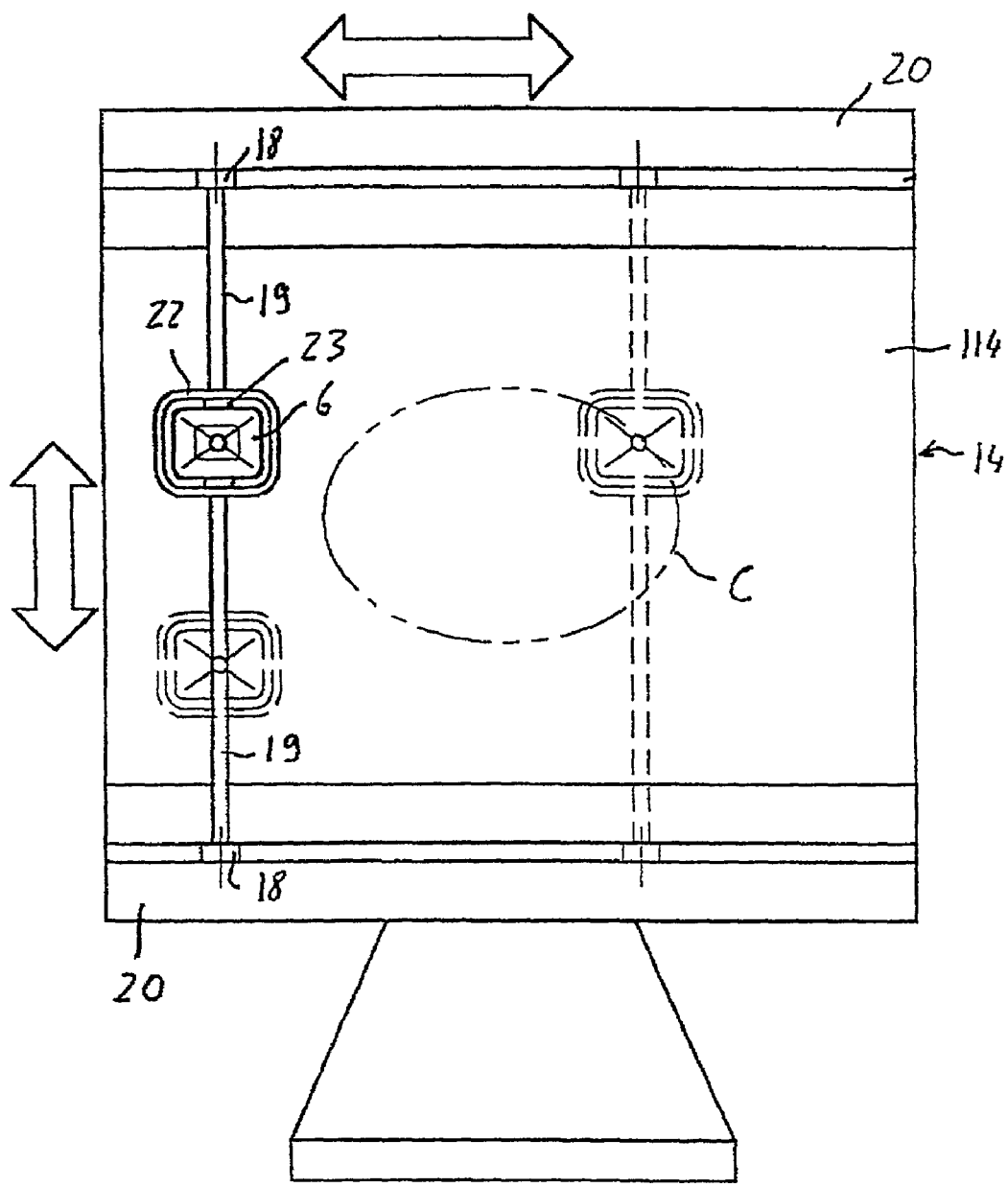
FIG. 10 is a front view as seen from the open side of the receiving coil as shown in FIG. 9.
Figure 11:
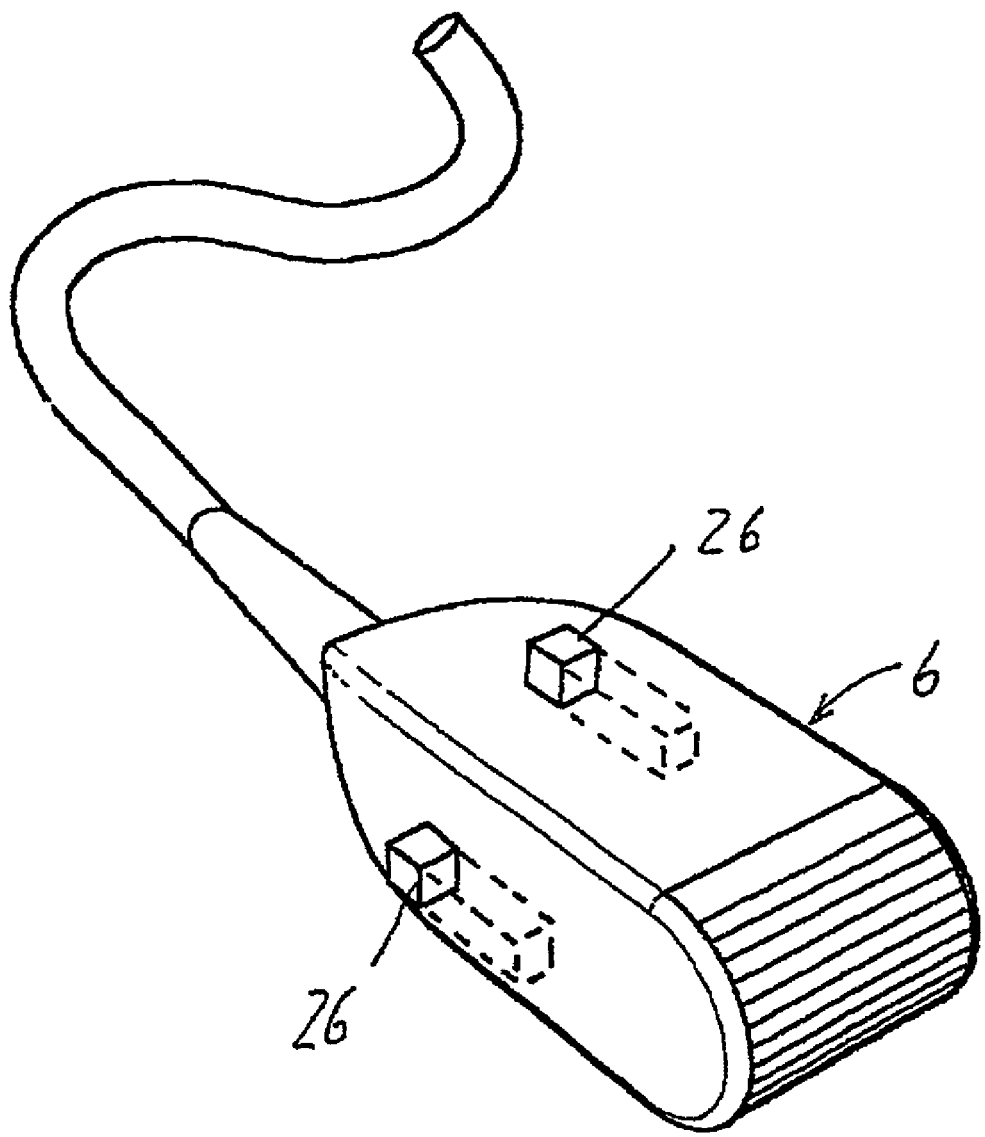
FIG. 11 shows an ultrasound imaging probe having marking elements adapted to generate a Nuclear Magnetic Resonance detectable signal.

Referring to FIGS. 9 to 11, a few arrangements are shown of the integrated apparatus of the invention. These arrangements are particularly advantageous with reference to apparatuses which integrate dedicated Nuclear Magnetic Resonance imaging devices, but may be obviously easily implemented with appropriate obvious modifications, to so-called total body or other similar apparatuses.

With reference to FIGS. 9 and 10, as is known, the low intensity of the transmitted MRI signals requires the receiving coil 14 to have such a size as to be as close as possible to the body part C under examination. The receiving coil 14 has an outer case or carter 114 for covering and finishing the magnetic structure 14, which is made of a material that does not interfere with MRI, generally plastic.

In this case, the receiving coil 14 is advantageously arranged to be open on at least one side, and is particularly made in the form of a sector of a cylindrical shell or the like, to allow the access, from said open side, of the ultrasonic probe 6 which, in the illustrated embodiment is of the type in which scanning is performed by mechanical displacement thereof along the anatomic part of the body C under examination. To this end, the ultrasonic probe 6 is provided with at least one pair of carriages 18 disposed at opposite ends of two support elements or arms 19 which are in turn disposed at opposite ends of the ultrasonic probe 6. The carriages are slidably engaged in a corresponding pair of guides 20 each disposed on one of the two delimiting edges of the opening of the part 114 for covering the receiving coil 14 and are oriented parallel to the axis of the receiving coil 14. Obviously, the opposite arrangement may be also provided, i.e., with the sliding carriages 18 being disposed on the edges of the opening, and the guides 20 being provided at the ends of the arms 19. Different slideable support means may be also provided. Particularly, besides the carriages 18 and the guides 20, the arms may be provided with an additional guide 22 for the slides 23 associated to the body of the probe 6 or to a support whereon the probe 6 may be secured. The guides 22 are oriented perpendicular to the axis of the receiving coil 14 and allow to bring the ultrasonic probe to contact with the region of the body C to be examined. Furthermore, the slides 23 may be attached to the probe 6 or to a support (not shown) in such a manner as to be able to rotate about an axis perpendicular to the sliding direction thereof, and to the sliding direction of the arms 19 along the guides 20.

Various means 24, 25 may be further provided to univocally define the mutual position between the ultrasonic probe 6, the part of the body C under examination and the receiving coil 14. Particularly, one or more light emitting elements may be fitted on the receiving coil, whose incident beam on the body surface has a light cone which indicates at least roughly the imaging area. These means may be of any type, i.e., may consist of a conventional light source associated to appropriately calibrated optical instruments or coherent light beams, such as laser beams having a harmless frequency or the like. The position and the displacements of the ultrasonic probe 6 may be read in several different manners, e.g. by means of encoders for detecting the angles of rotation and the number of revolutions completed by the driving motors, as known per se. Other means and methods, as known per se, are applicable, such as the combination of means for reading the resistance between conductors associated to the carriages 18 and to their respective guides 20, or code reading means associated to the guides 20 for reading codes disposed along the means 19 for supporting the probe 6, or vice versa there being provided the possibility to use either analog or digital optical means or electronic or electromechanical means.

In order to prevent any interference with the magnetic structure of the Nuclear Magnetic Resonance imaging device, said electric or optoelectronic tracer means may be enabled or disabled in a synchronized manner with the enabling and disabling of the ultrasound imaging device. Obviously, these tracer means may be also associated to the rotary support of the probe 6 (not shown), whereby they indicate the angular position of the probe. Obviously, the means for supporting the probe 6 may also be of a different type, and allow additional degrees of freedom in probe displacement.

According to the variant as shown in FIG. 11, one or more marking elements 26 may be provided on the body part C under examination and/or on the probe 6, which consist, for instance, of one or more bubbles of a liquid adapted to provide a typical Nuclear Magnetic Resonance response, for instance the so-called doped water, i.e., water mixed with other materials, such as oil.

Water bubbles generate clearly visible and easily recognizable spots in a Nuclear Magnetic Resonance image. This also allows to univocally recognize, possibly with the help of an image processing procedure, the position of the ultrasonic probe, regardless of whether it is simply hand held by the user, or supported by a structure as shown in FIG. 9. In this case, the arms 19 for slidably supporting the ultrasonic probe 6 have such a configuration that the ultrasonic probe 6 is positioned inside the cavity defined by the receiving magnet 14. It is apparent that the position of the probe 6 may be easily located by imaging the marking elements 26. To this end, the probe 6 need not be positioned in an area of the static magnetic field having such homogeneity conditions as to certainly provide diagnostically usable images, as markings are well visible even in poorer imaging accuracy conditions.

The marking elements may be arranged to not only indicate position, but even orientation of the ultrasonic probe 6, for instance they may have an elongated shape or consist of at least two bubbles or a row of bubbles aligned in a predetermined direction. Hence, the orientation of the alignment axis in the image obtained by Nuclear Magnetic Resonance imaging indicates the orientation of the scan plane of the ultrasonic probe 6.

An additional variant provides the use of magnetic means for marking and detecting the probe 6. To this end, the probe may be provided with elements 26 consisting of magnetic dipoles or Hall probes or combinations thereof, which interfere with a magnetic field. This method is already known to be used in combination with ultrasound imaging apparatuses. Advantageously, in the integrated apparatus of the invention, the magnetic structure of the ultrasound imaging device may be utilized as an element of the magnetic device for detecting the position of the ultrasonic probe 6 in combination with an appropriate processing electronics, which may be alternately connected to the circuits for controlling and processing Nuclear Magnetic Resonance signals to the magnetic structure when Nuclear Magnetic Resonance imaging is disabled.

These electronic circuits for detecting the position of the ultrasonic probe 6, as well as those associated to the different methods indicated above may be at least partly or wholly housed in the case of the magnetic structure or in the cabinet 202.

Figure 6:
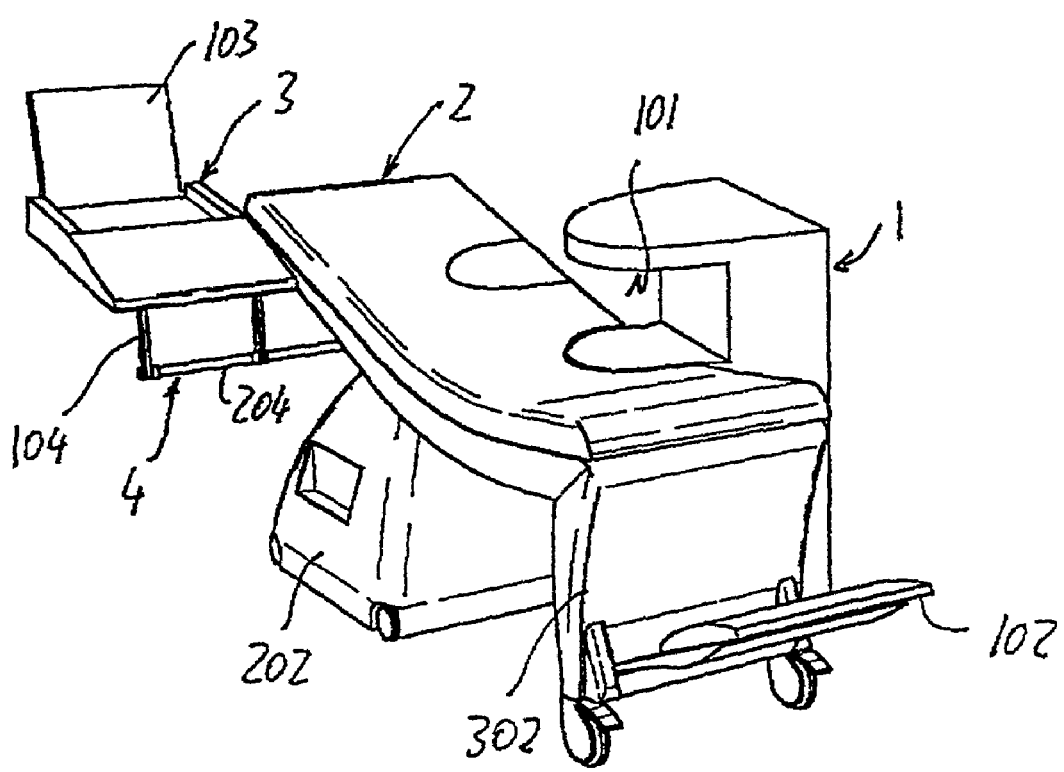
FIG. 6 shows a variant embodiment of the integrated apparatus as shown in FIGS. 1 to 5, in which the magnetic structure is very small and has an inverted U or C shape.
Figures 7, 8:
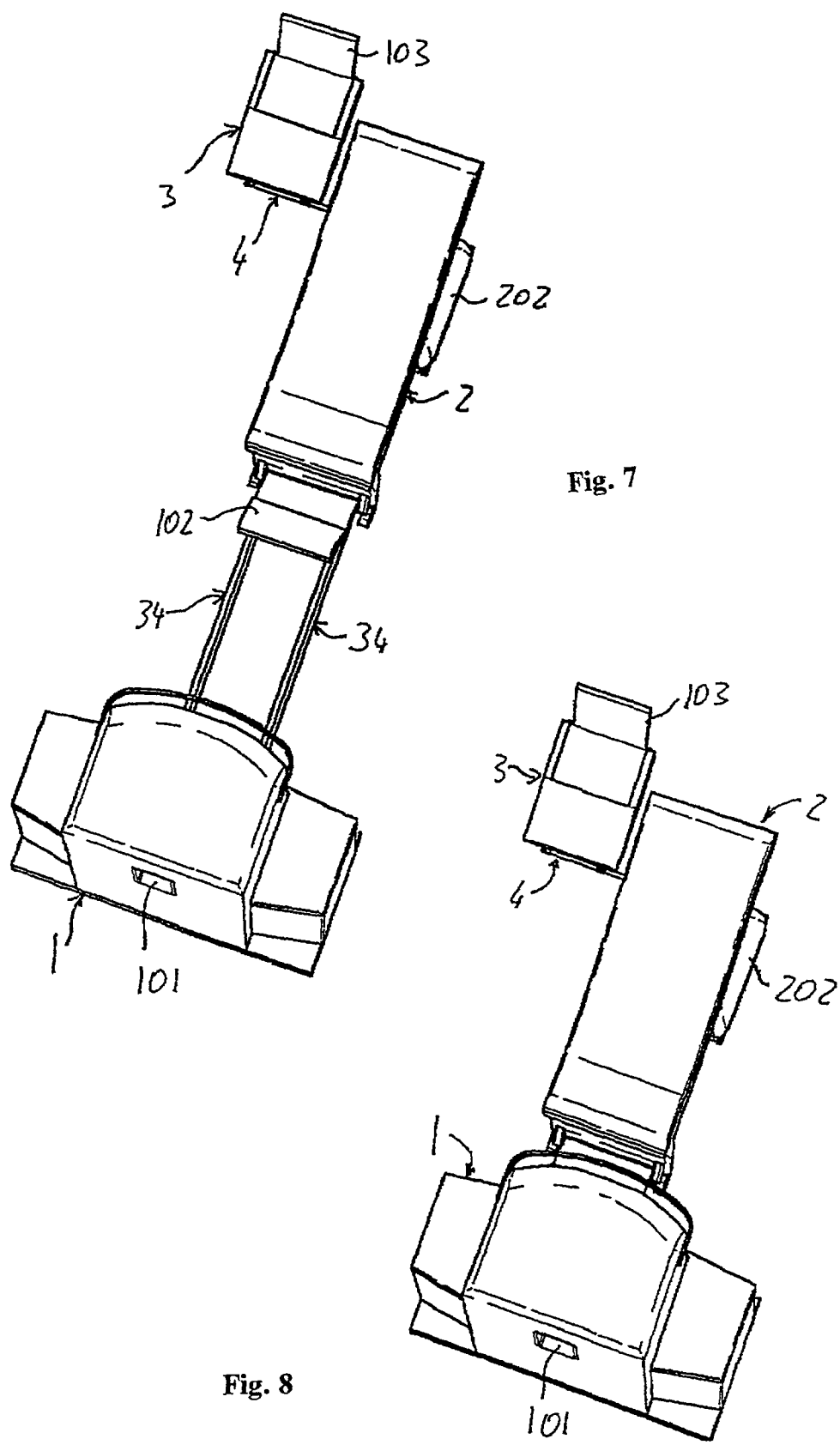
FIGS. 7 and 8 show a variant of the integrated apparatus, in which the magnetic structure of the Nuclear Magnetic Resonance imaging device is mounted with the table on a common guide for a controlled and measurable relative displacement.
Figure 13:
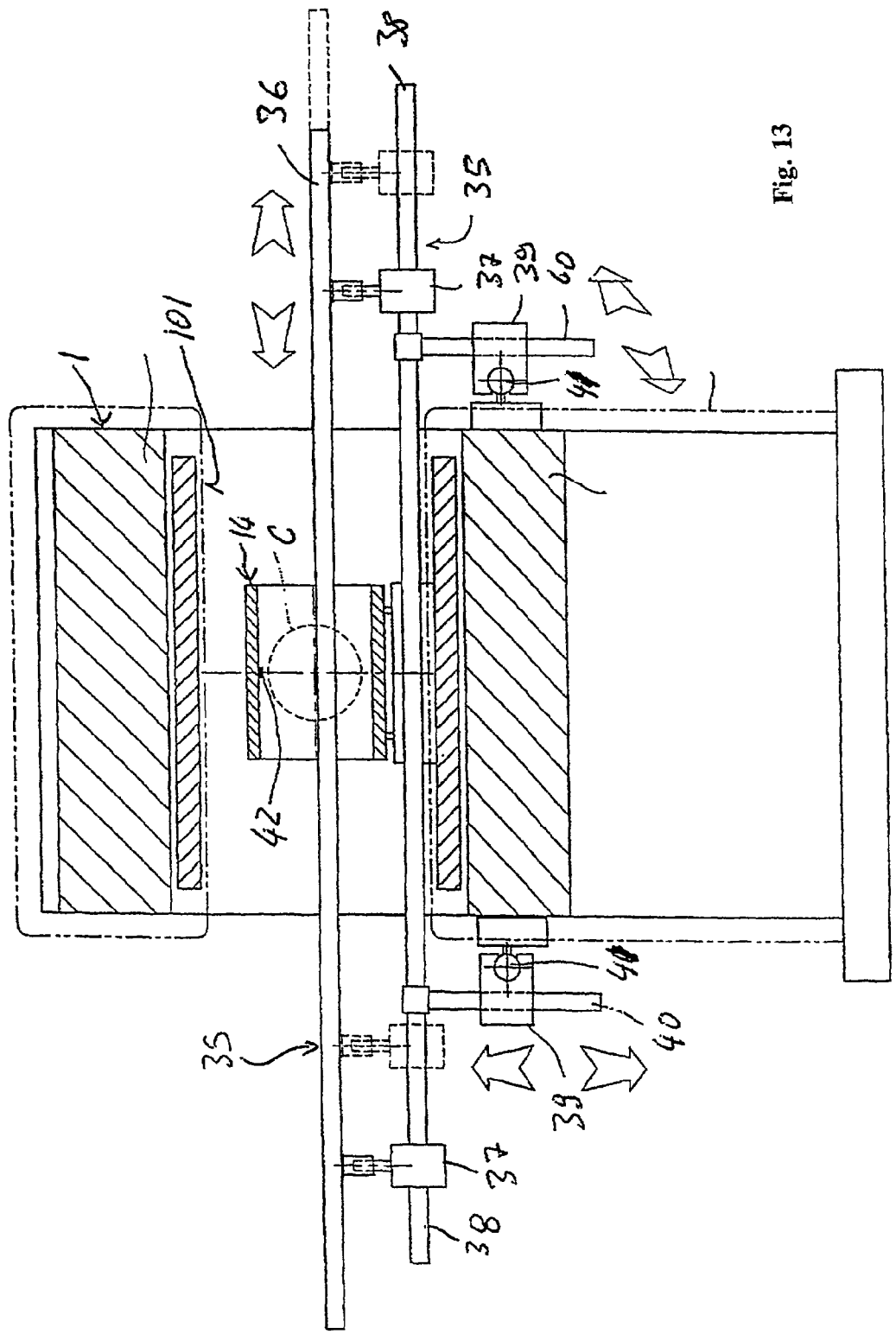
FIG. 13 is a schematic view of movable means for supporting a part of the patient body relative to the imaging volume, which are associated to the magnetic structure of the dedicated Nuclear Magnetic Resonance imaging device.
Figure 14:
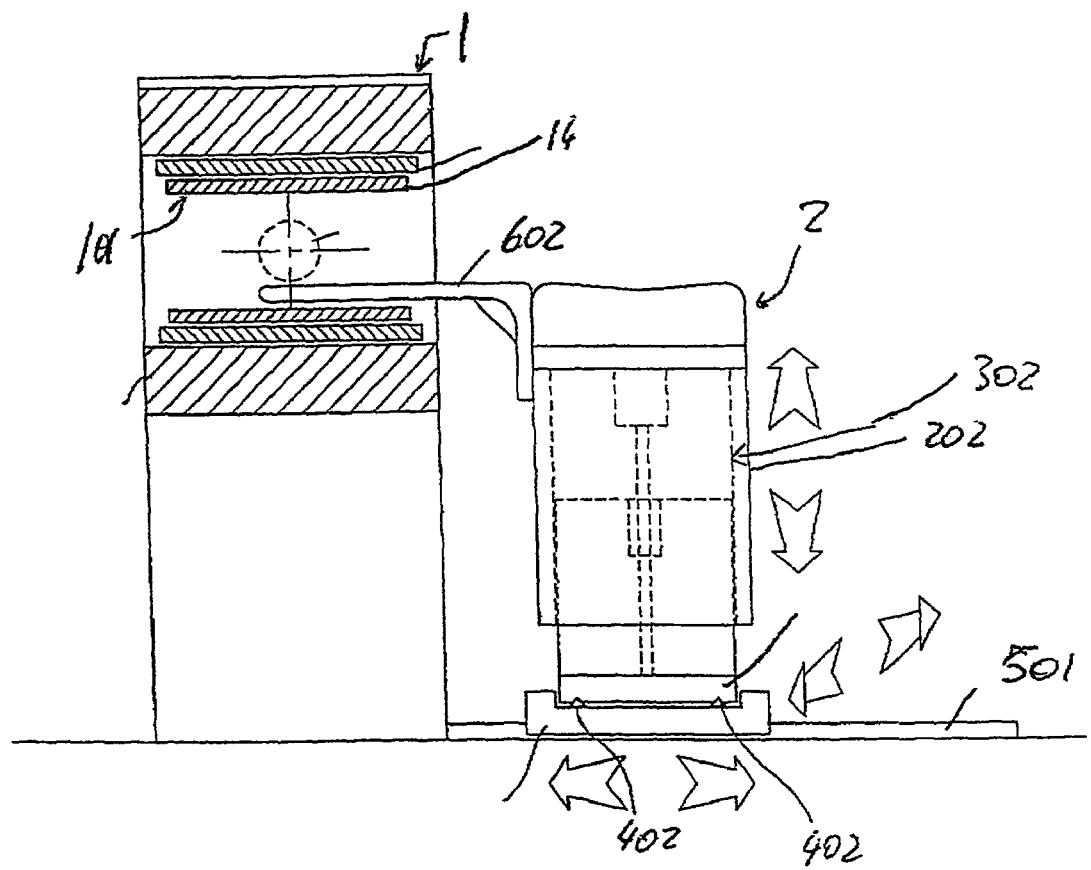
FIG. 14 shows a variant embodiment in which the receiving coil is integrated in the dedicated magnetic structure and has means for displacing the table relative to said magnetic structure.

Referring now to FIGS. 6, 13 and 14, a magnetic structure may be provided which is displaced relative to the patient table, hence to the body under examination or the part thereof C to a predetermined extent an in predetermined directions, the direction and displacement modulus being detected in the same manner as provided for the ultrasonic probe 6.

In this case, the magnetic structure 1 or the patient table 2, or both may be displaced relative to each other.

In the embodiment of FIGS. 6 and 14, there is provided at least one guide 34 on which the table 2 and/or the magnetic structure 1 and/or both are mounted to be displaced on slides or carriages.

Furthermore, the table 2 and/or the magnetic structure 1 and/or both may be arranged to rotate at least about a vertical axis.

The position locating means may be manufactured in the same manner as described for the ultrasonic probe 6 provided they are compatible with the magnetic structure 1.

With reference to FIGS. 13 and 14, two different arrangements are schematically shown, which are used to allow the magnetic structure 1 to be displaced relative to the body under examination, hence to the table 2, or to allow the table 2, hence the body under examination to be displaced relative to the magnetic structure 1, with respect to three spatial directions.

In this case the body under examination, the part thereof, the limb or the like is to be held in position so as to allow the displacement of the magnetic structure and the receiving coil with no mechanical interference with the magnetic structure and especially with the receiving coil. To this end, the magnetic structure 1, and/or the receiving coil 14 are associated to a support for the body, for the part thereof, for the limb or the like, which is displaceable relative to said structure and to said receiving coil. FIG. 13 is a schematic view of an embodiment of said support means, generally denoted by the numeral 35. In this case, the means for relative displacement of the magnetic structure 1 and of the body under examination are adapted to allow motion along orthogonal axes. Hence, even the movable support means are arranged to ensure displacement with respect to the magnetic structure along the same three orthogonal axes.

These support means may include a bearing member 36, such as a cradle, a surface, or the like which passes through the receiving coil 14 and slides at the outside ends of the magnetic structure on slides 36 mounted on guides 38 which are oriented parallel to the axis of the receiving coil, which is in turn parallel to a displacement axis. The guides 38 are supported on carriages 39, which are designed to slide on guides 40 orthogonal to the former and supported by a stationary member 101 of the case for the magnetic structure 1, which cannot be moved relative to the magnetic structure 1. The guide 40 is borne by guides 41, orthogonal to the guide 40 itself and to the guide 38 and is slidably engaged in the carriages 39. Hence, the body part under examination is perfectly still, whereas the magnetic structure moves together with the receiving coil 14.

According to an improvement, in order to allow at least a rough imaging of the region of the body under examination being imaged from time to time, one or more light emitting elements may be mounted on the receiving coil and/or on the magnetic structure, the cone of light of the beam incident on the body surface indicating the imaging portion. These means may be of any type, i.e., a conventional light source associated to appropriately calibrated optical instruments or coherent light beams, such as laser beams having a harmless frequency or the like. The Figure shows these light pointing means mounted on the receiving coil 14 and generally denoted by the reference number 42.

Obviously, some of the displacements in at least one of the directions or all of them may be performed by the table. In this case, the table is mounted on guides, like the magnetic structure. The embodiment of FIG. 14 schematically shows a variant, in which the base 202 of the table 2 has a vertical guide 302 and is mounted on orthogonal guides 402, 501, which have a predetermined starting position with respect to the magnet structure 1. In this embodiment, the receiving coil 14 is integrated in the magnetic structure 1.

Here, projecting cantilever means 602 are associated to the table 2 and carry the limb or the part of the body into the structure, thereby avoiding the complex construction of FIG. 13.

However, with reference to the embodiment of FIG. 6, the magnetic structure 1 has a very small size and is mounted on a carriage, whereas one of the poles thereof forms a portion of the support surface of the seat table 2. Such a magnet construction is well-known and forms the subject of a former published patent application EP 1004269.

The use of a construction of the magnetic structure 1 and of the table 2 as shown in FIG. 13 or 14, apparently allows to avoid the provision of separate means for guiding and displacing the ultrasonic probe 6 as described with reference to FIGS. 9 to 11. In this case, the probe may be fitted in a stationary position onto the receiving coil 14 or onto the magnetic structure 1, when the coil is integrated therein, and the displacement thereof occurs at the same time as the relative displacement between the magnetic structure 1 and the table 2. However, in this case, it might be advantageous to provide support means which allow to angularly displace the orientation of the probe 6 and/or to translate it away from or closer to the surface of the body under examination C.

As an alternative to the above mentioned case, the ultrasonic probe 6 may be separated from the receiving coil or the magnetic structure, or may be integrated, i.e., be a permanent part of the magnetic structure, by being incorporated therein or in the case of the receiving coil/s.

Obviously, when the characteristics as illustrated and described herein with reference to the different Figures and variants are not in contrast with each other, they may be provided in any combination, regardless of the expressly described and illustrated embodiments.

Figure 12:
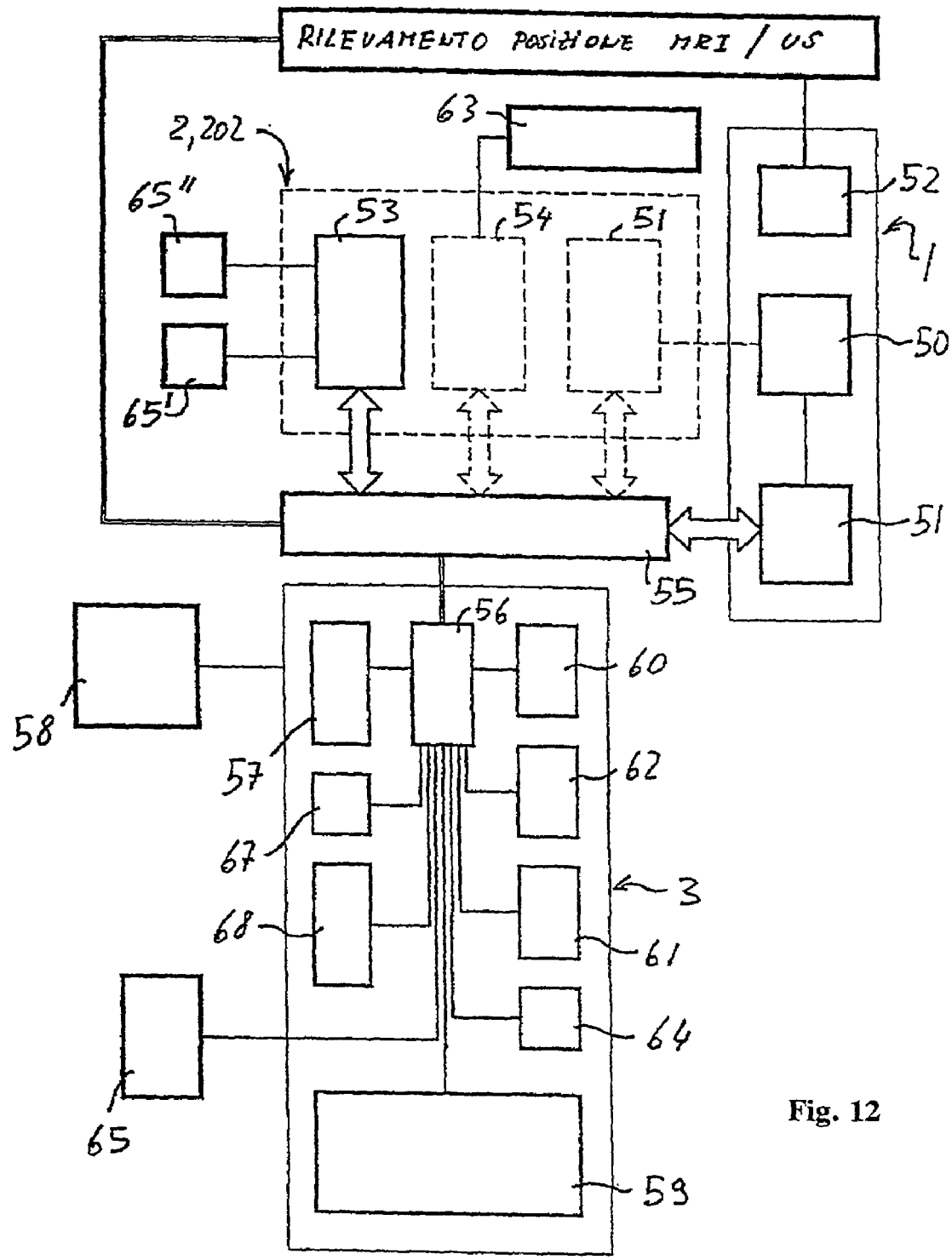
FIG. 12 shows a block diagram of the electronics for ultrasound imaging signal processing, as well as for controlling and processing and displaying the images obtained by the integrated apparatus as shown in the previous figures.

FIG. 12 shows a simplified block diagram of an example of a circuit for an integrated apparatus of the invention.

The Figure shows the magnetic structure 1, the patient table 2 and the console 3. The magnetic structure 1 includes the means for generating the static magnetic field and the various coils denoted as 50. A circuit 51 for controlling said means 50 and extracting from the received signals the data to be transformed into images, may be housed at least partly or wholly inside the magnetic structure containing case and/or at least partly or wholly in the structure of the table 2, particularly in the base block/cabinet 202.

The means 52 for controlling the relative position between the table and the magnetic structure and for processing the position reading may be disposed outside or integrated in the case for the magnetic structure and/or in the structure of the table 2, whereas both the means for controlling the transducers of the ultrasonic probe 6 and the means for receiving and processing the received signals to extract therefrom the data required for image reconstruction, generally denoted as 53, are integrated in the structure of the table 2 and particularly in the base block.

Possibly, the table structure 2 may integrate the control and dedicated processing circuits signals of devices for detecting further physiological parameters, such as ECG, EMG, EGG, and the circuits for synchronizing the ultrasound imaging and Nuclear Magnetic Resonance imaging processes with said parameters, which are shown with a dashed outline and denoted as 54.

The circuits 50, 51, 52, 53, 54 are connected to a data encoding unit for bidirectional communication with the console, a so-called bus, which is denoted as 55.

The bidirectional bus 55 is controlled by a microprocessor unit 56 of the console 3 and provides the image data obtained by the two methods and any additional parameter to the console 3. This data is transmitted to an image processing and display unit 57, hence to a display 58 or to another display device, such as a printer or the like. Also, the data may be stored into a mass storage memory, as a hard disk, or the like or on a floppy disk, or other removable memories such as a compactflash card, or recorded on a CD. Memories are denoted as 59. The console also includes memories 60, 61, 62, in which the software for controlling the various imaging options for each type of imaging mode are stored, e.g. for ultrasound imaging with B-Mode, Harmonic Imaging, Doppler, Color Doppler, etc., and/or for Nuclear Magnetic Resonance imaging with the different possible scan sequences or other typical adjustments or settings. The memory 62 represents the software for controlling devices having diagnostic purposes or for detecting any other physiological parameters, such as, without limitation, ECG, EMG, EGG devices.

The numeral 63 denotes the interfaces of said device with the patient.

The numeral 64 denotes a memory for programming therapeutic means or devices that may be used in combination with ultrasound and/or Nuclear Magnetic Resonance imaging means, and may use themselves ultrasounds or other types or radiation or intervention means, such as catheters, needles, ultrasonic means and needles, or else.

The numeral 65 denotes the ultrasonic probe and/or the therapeutic application tools. Possibly, as shown in 65' and 65", the probe and/or said devices may be directly connected to the control and processing circuits contained in the structure of the table 2.

The numerals 67 and 68 denote a scanner for digitizing images or else obtained by separate devices and additional data entry and/or control and/or display devices, etc., respectively.

Obviously, what has been described and illustrated with reference to FIG. 12 shall be intended without limitation. In fact, a global X-ray imaging or tomographic imaging device may be selected as an additional integrated device.

The structure of the integrated apparatus as described above allows to implement various imaging processes. First, all typical imaging modes of ultrasound and Nuclear Magnetic Resonance imaging apparatuses may be executed.

Further, the information obtained with the two imaging modes may be combined for comparison thereof, to achieve a safer recognition of irregular or pathological situations.

The two ultrasound and Nuclear Magnetic Resonance images may be also combined in such a manner as to reconstruct a more detailed image by mutually integrating the characteristics resulting from the two images.

The integrated apparatus in combination with the means for displacing the ultrasonic probe and the magnet relative to the region under examination allows to obtain tomographic and three-dimensional images of the body under examination or a part thereof, and hence to reconstruct a three-dimensional image based on the data obtained through the two different modes either by comparison or by integration.

Thanks to this method, the apparatus of the invention allows to perform a three-dimensional scan in a diversified manner for the two ultrasound and Nuclear Magnetic Resonance imaging types. Hence, for instance, according to a first variant, a three-dimensional tomographic scan may be executed, i.e., through several adjacent slice images of the body under examination or a part thereof, in which the distance between the individual slice images is different for the two imaging modes. Especially, the slice images may be closer to each other for the imaging mode which has shorter imaging times, whereas for the imaging mode with longer imaging times, the slice images are selected at a greater distance from each other.

Therefore, image reconstruction may integrate the data of an imaging method with that of the other method to perform interpolation reconstruction between two actually obtained adjacent slice images.

Within a single region of the body under examination in which imaging is to be performed in said two modes, it is also possible to use the more rapid imaging method in the lower interest peripheral areas of said region under examination and to use both imaging methods or only the other slower imaging method in the higher interest area of the region under examination.

In this case, the more rapid imaging method may be used to verify in real time that the region of interest has been reached so that the other imaging method may be enabled only in this condition, in combination with the other method or alone.

It shall be noted that, as mentioned in the previous description, in order to prevent any interference between the two imaging methods, and any resulting artifacts, the two methods may be enabled alternately in successive time intervals.

Imaging with the two methods also allows to locate the univocal space positions of the slice images obtained by each of the methods, with reference to an origin defined univocally at the beginning of the imaging session.

With reference to another variant of the method, the latter may include the steps of changing in real time, and during the imaging session, the imaging parameters according to the two methods, in such a manner as to change image quality characteristics, such as definition, field of view, signal-to-noise ratio, contrast.

In order to achieve this, the method provides that imaging parameters or imaging sequence settings are stored in the memories designed to contain the software for controlling the two imaging devices, which settings cause variations of said image quality characteristics, there being provided setting selectors which specifically indicate the modified image quality characteristics, rather than parameters or sequences.

Further, Nuclear Magnetic Resonance imaging methods may be implemented in combination with ultrasound imaging methods which have relatively short imaging times for a rough scan adapted to provide real-time displayable images for both imaging methods.

In this case, it is possible to reduce the definition and/or the field of view and/or the contrast and the signal-to-noise characteristics of the resulting image. Regarding the generation of artifacts caused by the use of less accurate scan modes, to the advantage of speed, it is initially possible to perform a comparative analysis between the images of the same slice obtained through the two methods to check if a certain structure represented in the image may or may not be an artifact. In this manner, the identification of artifacts is assured without affecting imaging speed.

According to a further improvement of the method, the combined imaging by the two imaging methods may be performed in combination with the injection of contrast agents in the region under examination.

It is possible to inject either contrast agents for ultrasounds (typically microbubbles) or contrast agents for Nuclear Magnetic Resonance (typically paramagnetic molecules). These contrast agents may be injected separately and alternately, or together, either separately or in the form of a mixture.

Advantageously, the two types of contrast agents may be combined together by using a single carrier for the two. As an alternative, the carrier for the one may have the contrast agent characteristics required for the other imaging mode. Particularly, the microbubble carrier may have the paramagnetic characteristics required for Nuclear Magnetic Resonance imaging contrast agents.

Nuclear Magnetic Resonance contrast agents may be also arranged to be contained inside micro-bubbles.

When the two contrast agents are used in combination, the advantage is obtained that one of the two imaging methods, i.e., the more rapid method, adapted to provide real-time images may be used to identify with a higher accuracy the instant in which the region under examination is reached by the contrast agents for the other generally slower imaging method. Typically, Nuclear Magnetic Resonance imaging requires longer times to display the resulting image, whereby ultrasound imaging allows to monitor the perfusion condition of the region under examination, and prevents Nuclear Magnetic Resonance imaging of said region from occurring when the specific contrast agents are still not or no longer present in the region under examination. These early or late imaging situations may jeopardize the examination and require the repetition thereof, while involving a repeated invasive operation on the patient, as well as time loss and power and material consumption.

In combination with or as an alternative to said contrast agents, substances may be used that are adapted to determine a higher oxygen request in the region under examination, hence an increase of blood flow.

Imaging by the two methods may be synchronized with the heart cycle of the patient, by providing the steps of detecting the electrocardiogram of the patient and of defining the curve thereof, wherewith imaging with one of the two imaging methods or with both imaging methods is synchronized. Synchronization with the heart cycle may be also adjusted in such a manner that one of the two imaging types is synchronized with a predetermined phase of the heart cycle and the other with another phase.

By synchronizing imaging with the heart cycle according to the two different imaging methods the two imaging types may be executed in identical physiological conditions. This may be very useful when imaging is aimed at examining spontaneous flows, such as the blood flow, or the like.

The option to also provide other means for imaging or detecting other physiological parameters, to be integrated in the same apparatus allows to relate images of the region under examination with other types of examinations and to possibly establish relations between the results thereof and the resulting images. This may be useful to identify any possible artifact, as well as any possible connection between the obtained images and the detected values for the different physiological parameters or other types of images.

As an additional image type, an X-ray imaging device may be integrated with the ultrasound and Nuclear Magnetic Resonance imaging devices. In this case, the XR device is also enabled in different periods from those of the other two imaging devices and the obtained, digitized and stored images may be used to integrate, correct or evaluate the information obtained by the other two imaging methods.

Obviously, the invention is not limited to what has been described and illustrated herein, but may be greatly varied. Variations may particularly relate to the combination of not expressly mentioned imaging techniques or with not expressly mentioned means for detecting physiological parameters, as well as to the combination with other ultrasound and/or Nuclear Magnetic Resonance imaging signal detection and processing. The invention may be also greatly varied and modified as regards construction. All the above without departure from the inventive teaching disclosed above and claimed below.

The invention claimed is:

1. A combined apparatus for imaging an inner part of a body, comprising an integrated configuration that includes:
   a nuclear magnetic resonance imaging and displaying device, and
   an ultrasound imaging and displaying device;
   and in which the nuclear magnetic imaging and displaying device and ultrasound imaging and displaying device each comprises:
   a dedicated means for generating waves or beams which are transmitted toward the part of the body to be internally imaged;
   a dedicated means for receiving said waves or beams transmitted from the part of the body under examination or waves or beams deriving from the excitation of the part of the body under examination;
   a circuit configured to relate the information of the waves or beams transmitted from the part of the body under examination to a space position for each of a plurality of image unit elements; and
   a circuit configured to construct an image from the image unit elements obtained thereby, which turn the information of the received waves or beams into brightness and/or color characteristics of the individual image unit elements of the image;
   wherein the ultrasound imaging device comprises an ultrasonic probe for transmitting and receiving ultrasonic waves, and
   further comprising a magnetic structure forming a cavity for receiving the body under examination or a part thereof and adapted to receive the ultrasonic probe at the edges of the cavity and means for locating the position and/or the orientation of the ultrasonic probe relative to the body or the part thereof under examination; and
   wherein the magnetic structure includes a receiving coil associated thereto and said magnetic structure or receiving coil has combinations of guides or slides for displacing the ultrasonic probe in at least one direction which are associated with a tracer means for reading the position along the directions of the ultrasonic probe.

2. The apparatus as claimed in claim 1, wherein the apparatus includes:
   electronic control, processing and data storage circuits,
   a patient supporting element,
   a case for at least one control and display console, shared by the imaging devices integrated therein,
   a case for a magnetic structure, and
   wherein at least one of the patient supporting element, the case of the control and display console, and the case of the magnetic structure includes chambers for housing completely, or at least partly, the electronic control, processing and data storage circuits.

3. The apparatus as claimed in claim 1, wherein electronic circuits of the nuclear magnetic resonance imaging devices and electronic circuits of the ultrasound imaging device are divided into separate blocks, at least one block being made of circuits for controlling, receiving and processing the beams, waves or signals transmitted to the body under examination and the signals coming from the body under examination according to a particular imaging type, and another block of circuits being made of circuits for entering commands, generating and processing images, and for displaying and/or storing data, said other block of circuits including transmitting and receiving circuits which encode the signals whereby the two blocks communicate in an identical and compatible manner.

4. The apparatus as claimed in claim 3, wherein the apparatus comprises a common console including common circuits for generating and/or processing and/or displaying and/or storing the images and/or a plurality of physiological parameters obtained for each imaging type integrated therein or provided in combination, the console being provided with means for entering specific commands for each type of imaging devices, which means may be dedicated to the specific imaging device and/or shared by all imaging devices.

5. The apparatus as claimed in claim 1, further comprising an X-Ray imaging and displaying device.

6. The apparatus as claimed in claim 1, further comprising at least one additional type of device for detecting and measuring physiological parameters, said additional type of device being at least one of a device for detecting an EGG and/or EGG and/or EMG electrocardiogram.

7. The apparatus as claimed in claim 6, wherein the circuit for synchronizing the enabling/disabling functions for the imaging devices is connected to the output of at least one of the devices for detecting physiological parameters and particularly to an electrocardiograph, to control the enabling and/or disabling functions for the different imaging devices or of devices for detecting any other physiological parameters in such a manner as to synchronize them with certain values or curves of at least one of the physiological parameters.

8. The apparatus as claimed in claim 1, further comprising a circuit for synchronizing enabling and/or disabling functions for the different imaging devices which may be controlled by a console.

9. The apparatus as claimed in claim 8, wherein the synchronization circuit enables the individual imaging devices in an alternate manner and for intervals of a predetermined duration.

10. The apparatus as claimed in claim 1, wherein the means for locating the position and/or orientation of the ultrasonic probe consist of marking elements provided on the probe itself, which are visible in the Nuclear Magnetic Resonance image.

11. The apparatus as claimed in claim 10, wherein the probe has a plurality of marking elements, aligned at least in pairs in one of three orthogonal spatial directions.

12. The apparatus as claimed in claim 10, wherein the marking elements have an elongated shape with the longitudinal axis being aligned in at least one of three orthogonal spatial directions.

13. The apparatus as claimed in claim 1, wherein the means for locating the position and/or orientation of the ultrasonic probe comprise magnetized elements and/or magnetic sensors which are secured or associated to the ultrasonic probe and to the magnetic structure.

14. The apparatus as claimed in claim 1, wherein the tracer means comprises optoelectronic position reading means, or bar codes readers for indicating the position along a translation or displacement path and/or of electronic or electrical position reading means.

15. The apparatus as claimed in claim 1, wherein the magnetic structure may be displaced in at least one direction relative to the body under examination or a part thereof, and further comprising means for locating the relative position between the magnetic structure and the body under examination.

16. The apparatus as claimed in claim 15, wherein the magnetic structure may be displaced relative to a table, chair or table/chair or vice versa, and is mounted on combinations of guides and carriages which are linked to the table, chair or table/chair.

17. The apparatus as claimed in claim 16, wherein tracer means for locating the relative position and/or orientation between the table, chair or table/chair and the magnetic structure are associated to the combination of guides or carriages for displacing the magnetic structure and/or the table, chair or table/chair.

18. The apparatus as claimed in claim 16, wherein the magnetic structure and/or the table, chair or table/chair may be freely displaced relative to each other, there being provided tracer or sensor means.

19. The apparatus as claimed in claim 18, further comprising means for locating a relative position between the magnetic structure and the body under examination or a part thereof which are removable and may be positioned on said body under examination or a part thereof.

20. The apparatus as claimed in claim 16, wherein the magnetic structure is dedicated and has a small size as compared with the chair, table, or table/chair, a portion of the patient supporting surface of said chair, table, or table/chair being formed by at least a portion of said magnetic structure.

21. The apparatus as claimed in claim 1, wherein the magnetic structure and/or the receiving coil have means for supporting the body under examination or a part thereof, which may be displaced relative to said magnetic structure and/or to the receiving coil.

22. The apparatus as claimed in claim 1, wherein the receiving coil has an annular or substantially cylindrical shape, the ultrasonic probe being housed in a case thereof, and said receiving coil being displaceable with the magnetic structure in at least one direction relative to the body under examination or a part thereof.

23. An imaging method comprising:
providing the integrated apparatus as claimed in claim 1:
acquiring a first image type;
acquiring a second image type;
generating a first image type; and
generating a second image type;
wherein the first image type and the second image type are acquired alternately in successive intervals.

24. The method as claimed in claim 23, wherein the first image type and the second image type are ultrasound imaging and Nuclear Magnetic Resonance imaging.

25. The method as claimed in claim 23, wherein the apparatus includes a processor configured to have dedicated processing of the two image types, configured to reconstruct a set of image data, configured to convert said image data into data encoded according to a predetermined communication protocol, configured to transmit said image data to an image processing and displaying station which is shared or essentially shared by the two different imaging types, and which processes and displays the images obtained by said two imaging types, in adjacent, subsequent, overlaid and/or combined positions, thereby constructing a single image from the information of said two images obtained by the two different imaging types.

26. The method as claimed in claim 23, further comprises successive imaging of slices of the body under examination or a part thereof, univocally locating the position and orientation in space for each slice image and reconstructing a three-dimensional image formed by the individual slice images.

27. The method as claimed in claim 23, further comprises successive imaging of the body under examination or a part thereof by the at least two imaging types and reconstructing two three-dimensional images by said two imaging types and/or display of the two images in an overlaid position and/or combination of the two three-dimensional images into a common three-dimensional image formed by the information of both three-dimensional images obtained by the two imaging types.

28. The method as claimed in claim 23, further comprising obtaining the slice images for the two imaging types along coincident slice planes of the body under examination or a part thereof.

29. The method as claimed in claim 23, further comprising obtaining the slice images for the two imaging types along non-coincident slice planes of the body under examination or a part thereof.

30. The method as claimed in claim 23, further comprising injecting contrast agents for ultrasound images, and ultrasound imaging thereof.

31. The method as claimed in claim 23, further comprising injecting contrast agents for Nuclear Magnetic Resonance images, and imaging thereof.

32. The method as claimed in claim 23, further comprising injecting contrast agents for ultrasound images and for Nuclear Magnetic Resonance images, whereas the moment in which the Nuclear Magnetic Resonance contrast agents reach the region of interest for imaging purposes is determined by detecting the moment in which the region of interest is reached by ultrasound imaging of ultrasound contrast agents, or vice versa.

33. The method as claimed in claim 23, further comprises providing a variation of the imaging parameters for one and/or for the other of the two imaging types, for a higher or lower image quality or longer or shorter imaging times based on the coincidence of an image plane with regions of higher or lower interest for the one and/or the other imaging type.

* * * * *